United States Patent
Satoh

(10) Patent No.: US 11,234,679 B2
(45) Date of Patent: Feb. 1, 2022

(54) ULTRASOUND DIAGNOSTIC APPARATUS AND ULTRASOUND IMAGE PRODUCING METHOD

(71) Applicant: FUJIFILM Corporation, Tokyo (JP)

(72) Inventor: Yoshiaki Satoh, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 444 days.

(21) Appl. No.: 16/403,907

(22) Filed: May 6, 2019

(65) Prior Publication Data

US 2019/0254636 A1 Aug. 22, 2019

Related U.S. Application Data

(60) Division of application No. 14/264,603, filed on Apr. 29, 2014, now Pat. No. 10,321,895, which is a
(Continued)

(30) Foreign Application Priority Data

Nov. 10, 2011 (JP) ................................. 2011-246309
Aug. 20, 2012 (JP) ................................. 2012-181612

(51) Int. Cl.
*A61B 8/14* (2006.01)
*A61B 8/08* (2006.01)
(Continued)

(52) U.S. Cl.
CPC .......... *A61B 8/5207* (2013.01); *A61B 8/4438* (2013.01); *A61B 8/4488* (2013.01);
(Continued)

(58) Field of Classification Search
None
See application file for complete search history.

(56) References Cited

U.S. PATENT DOCUMENTS

| 4,135,139 A | 1/1979 | Buchner |
| 6,595,921 B1 | 7/2003 | Urbano et al. |

(Continued)

FOREIGN PATENT DOCUMENTS

| JP | 9-75350 A | 3/1997 |
| JP | 2004-41273 A | 2/2004 |

(Continued)

OTHER PUBLICATIONS

International Search Report, dated Jan. 15, 2013, issued in PCT/JP2012/077348.

(Continued)

*Primary Examiner* — Luther Behringer
(74) *Attorney, Agent, or Firm* — Birch, Stewart, Kolasch & Birch, LLP

(57) ABSTRACT

In an ultrasound diagnostic apparatus of the present invention, the controller writes and reads element data of one frame into and out from two or more buffer memories 21a, 21b, ... 21i sequentially frame by frame and assigns the element data of one frame sequentially read out from the buffer memories to a plurality of arithmetic blocks of a signal processor, wherein the element data assigned is subjected to processing by each of a plurality of arithmetic cores in the plurality of arithmetic blocks to produce an image signal.

8 Claims, 10 Drawing Sheets

Related U.S. Application Data continuation of application No. PCT/JP2012/077348, filed on Oct. 23, 2012.

(51) Int. Cl.
*A61B 8/00* (2006.01)
*A61B 5/00* (2006.01)
*A61B 5/145* (2006.01)

(52) U.S. Cl.
CPC ............... *A61B 8/486* (2013.01); *A61B 8/56* (2013.01); *A61B 5/0095* (2013.01); *A61B 5/14542* (2013.01)

(56) References Cited

U.S. PATENT DOCUMENTS

| | | | |
|---|---|---|---|
| 8,157,738 B2* | 4/2012 | Wegener | A61B 8/483 600/443 |
| 8,317,706 B2* | 11/2012 | Wegener | A61B 8/06 600/443 |
| 2002/0173721 A1 | 11/2002 | Grunwald et al. | |
| 2003/0153824 A1 | 8/2003 | Tsubata | |
| 2004/0015079 A1 | 1/2004 | Berger et al. | |
| 2005/0093859 A1 | 5/2005 | Sumanaweera et al. | |
| 2009/0171214 A1 | 7/2009 | Kim et al. | |
| 2010/0246665 A1 | 9/2010 | Brederson et al. | |
| 2012/0310095 A1 | 12/2012 | Sato | |

FOREIGN PATENT DOCUMENTS

| | | |
|---|---|---|
| JP | 2006-174902 A | 7/2006 |
| JP | 2009-160401 A | 7/2009 |

OTHER PUBLICATIONS

Japanese Office Action, dated Apr. 14, 2015, for Japanese Application No. 2012-181612, along with a Partial English translation.
Machine Translation of JP 09-075350; retrieved Nov. 21, 2017.

* cited by examiner

ULTRASOUND DIAGNOSTIC APPARATUS AND ULTRASOUND IMAGE PRODUCING METHOD

CROSS REFERENCE TO RELATED APPLICATIONS

This application is a Division of copending U.S. application Ser. No. 14/264,603, filed Apr. 29, 2014, (now U.S. Pat. No. 10,321,895 issued Jun. 18, 2019), which is a continuation application of International Application PCT/JP2012/077348 filed on Oct. 23, 2012, which claims priority under 35 U.S.C. 119(a) to Application No. 2011-246309 filed in Japan on Nov. 10, 2011 and Application No. 2012-181612 filed in Japan on Aug. 20, 2012, all of which are hereby expressly incorporated by reference in their entirety into the present application.

BACKGROUND OF THE INVENTION

The present invention relates to an ultrasound diagnostic apparatus and an ultrasound image producing method and particularly to an ultrasound diagnostic apparatus having a battery to supply power to each component of an ultrasound probe and a diagnostic apparatus body.

Conventionally, ultrasound diagnostic apparatuses using ultrasound images have been employed in the medical field. In general, this type of ultrasound diagnostic apparatus comprises an ultrasound probe having a built-in transducer array and an apparatus body connected to the ultrasound probe. The ultrasound probe transmits an ultrasonic beam toward the inside of a subject's body, receives ultrasonic echoes from the subject, and the apparatus body electrically processes the reception signals to produce an ultrasound image.

In such ultrasound diagnosis, various examinations such as B-mode examination, M-mode examination, CF-mode examination and PW-mode examination are performed. In recent years, an ultrasound diagnostic apparatus capable of those examinations has been reduced in size by adopting an application specific integrated circuit (ASIC) or a processor and is applied as a mobile ultrasound diagnostic apparatus, for example. However, when those various examinations are carried out by a single apparatus, since signal processing, image processing or other processing requires many arithmetic operations, there is a problem that processing speed of the apparatus decreases.

As a technology for improving the processing speed, ultrasound diagnostic apparatuses which perform parallel arithmetic operations using a large number of arithmetic cores in signal processing and the like have been proposed, as disclosed in JP 2006-174902 A.

The apparatus disclosed in JP 2006-174902 A divides a measurement region into plural regions in a scanning line direction, and assigns an arithmetic core to each of the divided regions, whereby image processing is carried out in a parallel fashion in the scanning line direction, and thus the processing speed can be improved.

However, there is a demand for further improvement of processing speed in the recent ultrasound diagnosis which is becoming more and more complicated, like in the case where two or more examinations such as B-mode examination, CF-mode examination and PW-mode examination are simultaneously executed.

SUMMARY OF THE INVENTION

The present invention has been made to solve the above-described problem of the prior art and has an object to provide an ultrasound diagnostic apparatus and an ultrasound image producing method that can improve the processing speed in producing an ultrasound image.

The ultrasound diagnostic apparatus according to the present invention comprises: a transducer array; a transmission circuit configured to transmit an energy beam toward a subject; a reception circuit configured to process a reception signal outputted from the transducer array that received ultrasonic waves generated from the subject upon transmission of the energy beam to thereby generate element data; two or more buffer memories into each of which element data of one frame is written; a signal processor constituted with a plurality of arithmetic blocks each including a plurality of arithmetic cores and configured to produce an image signal through processing of the element data of one frame read out from each of the buffer memories by the plurality of arithmetic cores in the plurality of arithmetic blocks; and a controller configured to write and read element data into and out from the two or more buffer memories sequentially frame by frame and to assign the element data of one frame read out to the signal processor to the plurality of arithmetic blocks sequentially, to thereby cause the plurality of arithmetic cores to perform processing on the element data.

In B-mode processing, the controller can assign the element data of one frame to the plurality of arithmetic blocks for every plurality of scanning lines, defines a plurality of divisional regions formed by dividing a measurement region in a depth direction for each of the arithmetic blocks, and assigns the divisional regions to the arithmetic cores one by one.

The controller can assign CF-mode processing and B-mode processing to the plurality of arithmetic blocks. The controller can assign CF-mode processing, PW-mode processing and B-mode processing to the plurality of arithmetic blocks. In addition, the controller can assign CF-mode processing, PW-mode processing, B-mode processing and M-mode processing to the plurality of arithmetic blocks.

In B-mode processing, the controller can control the transmission circuit and the reception circuit to transmit and receive ultrasonic waves in different directions from one another and performs spatial compounding in each of the plurality of arithmetic blocks.

Preferably, each of the plurality of arithmetic blocks includes a super function unit, and the controller causes the super function unit included in each of the arithmetic blocks to perform frequency analysis in CF-mode processing.

Preferably, the energy beam is one of an ultrasonic beam and an irradiation light beam.

The ultrasound image producing method according to the present invention comprises the steps of: emitting an energy beam toward a subject; receiving by a transducer array ultrasonic waves generated from the subject upon transmission of the energy beam; generating element data by processing in a reception circuit a reception signal outputted from the transducer array that has received the ultrasonic waves; writing element data of one frame into each of two or more buffer memories in such a manner that the two or more buffer memories correspond to frames one by one; producing an image signal by assigning the element data of one frame sequentially read out from the buffer memories to a plurality of arithmetic blocks, and causing each of a plurality of arithmetic cores included in the plurality of arithmetic blocks to perform processing on the element data of one frame assigned; and repeating writing and reading element data into and out from the two or more buffer memories frame by frame.

According to the present invention, element data is alternately written into and read out from two buffer memories for every frame, and the read-out element data of one frame is assigned to a plurality of arithmetic blocks to be processed, whereby the processing speed in producing an ultrasound image can be improved.

DETAILED DESCRIPTION OF THE INVENTION

Embodiments of the present invention will be described below based on the appended drawings.

Embodiment 1

Figure 1:
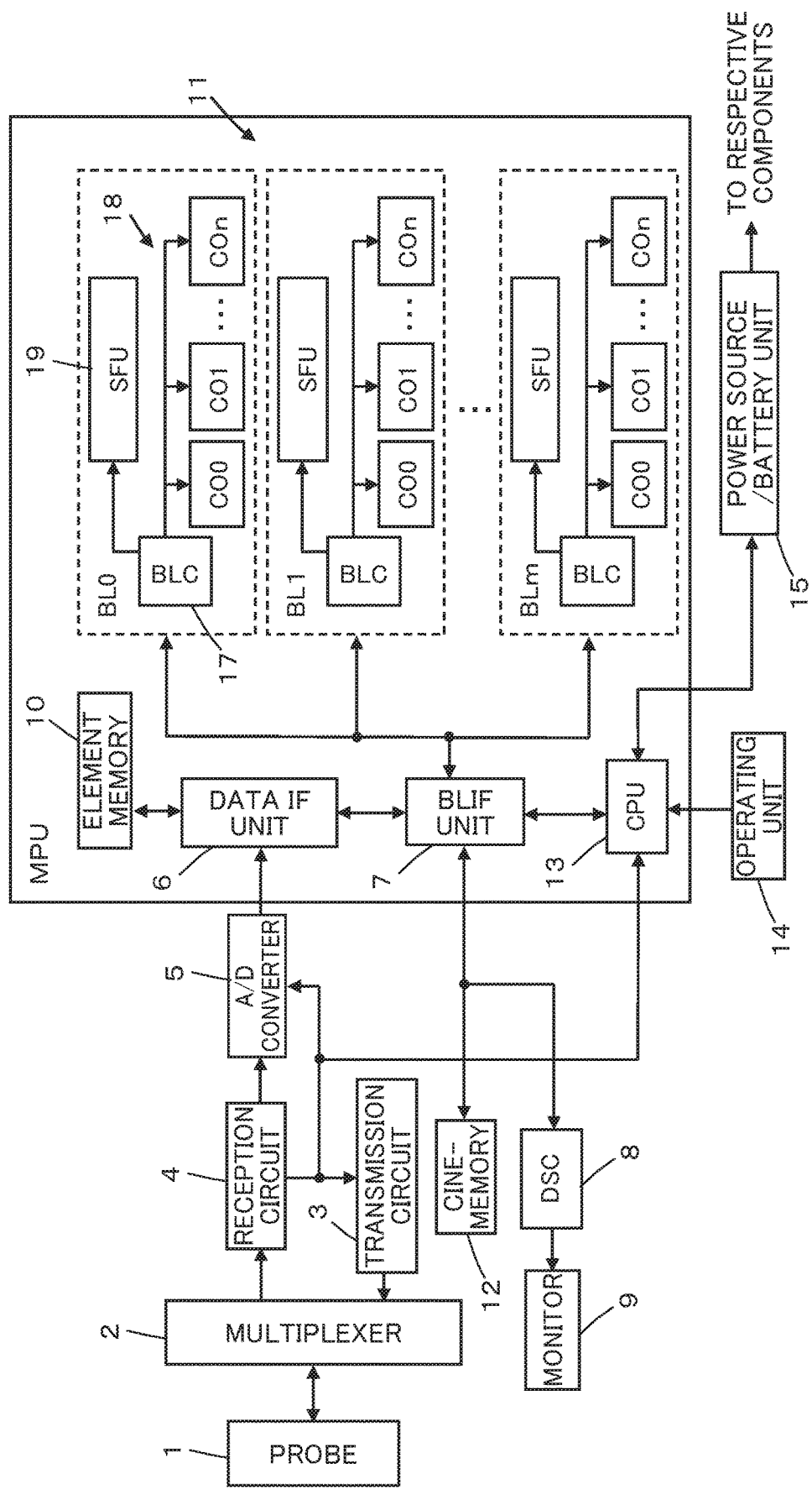
FIG. 1 is a block diagram illustrating a configuration of an ultrasound diagnostic apparatus according to Embodiment 1 of the invention.

FIG. 1 illustrates a configuration of an ultrasound diagnostic apparatus according to Embodiment 1 of the invention. The ultrasound diagnostic apparatus includes a probe 1, which is connected to a transmission circuit 3 and a reception circuit 4 via a multiplexer 2. The reception circuit 4 is connected to an A/D converter 5, a data interface (IF) unit 6, a block interface (BLIF) unit 7, a digital scan converter (DSC) 8 and a monitor 9 in order, and the data IF unit 6 is connected to an element memory 10, while the BLIF unit 7 is connected to a signal processor 11 and a cine-memory 12.

The transmission circuit 3, the reception circuit 4, the A/D converter 5 and the BLIF unit 7 are connected to a CPU 13. The CPU 13 is also connected to an operating unit 14 and a power source/battery unit 15.

The probe 1 includes a transducer array in which a plurality of transducer elements are arranged one-dimensionally or two-dimensionally. These transducer elements each transmit ultrasonic waves according to transmission pulses supplied from the transmission circuit 3 via the multiplexer 2 and receive ultrasonic echoes from the subject to output reception signals. Each of the transducer elements comprises a vibrator composed of a piezoelectric body and electrodes each provided on both ends of the piezoelectric body. The piezoelectric body is composed of, for example, a piezoelectric ceramic represented by a lead zirconate titanate (PZT), a piezoelectric polymer represented by polyvinylidene fluoride (PVDF), or a piezoelectric monochristal represented by lead magnesium niobate lead titanate solid solution (PMN-PT).

When the electrodes of each of the vibrators are supplied with a pulsed voltage or a continuous-wave voltage, the piezoelectric body expands and contracts to cause the vibrator to produce pulsed or continuous ultrasonic waves. These ultrasonic waves are combined to form an ultrasonic beam (energy beam). Upon reception of propagating ultrasonic waves, each vibrator expands and contracts to produce an electric signal, which is then outputted as a reception signal of the ultrasonic waves.

The multiplexer 2 selects transducer elements to be used in a single transmission, connects the selected transducer elements to the transmission circuit 3 at the timing of transmission, and connects the transducer elements to the reception circuit 4 at the timing of reception.

The transmission circuit 3 includes, for example, a plurality of pulsers, adjusts the delay amounts for the respective transmission pulses based on a transmission delay pattern selected according to an instruction signal transmitted from the CPU 13 such that the ultrasonic waves transmitted from a plurality of transducers of the probe 1 form an ultrasonic beam, and supplies the transducers with delay-adjusted transmission pulses.

In accordance with the instruction signal from the CPU 13, the reception circuit 4 amplifies reception signals transmitted from the respective elements of the transducer array.

In accordance with the instruction signal from the CPU 13, the A/D converter 5 performs A/D conversion on the reception signals amplified in the reception circuit 4 to generate element data. Under the control of the CPU 13, the data IF unit 6 communicates between the A/D converter 5 and the element memory 10 or between the element memory 10 and the BLIF unit 7. The element memory 10 stores element data generated by the A/D converter 5 sequentially via the data IF unit 6. Under the control of the CPU 13, the BLIF unit 7 communicates between the signal processor 11 and the data IF unit 6, the cine-memory 12 or the DSC 8.

The signal processor 11 comprises a plurality of blocks 16 (BL0 to BLm) connected in parallel to the BLIF unit 7. Each of the blocks includes a block controller (BLC) 17 connected to the BLIF unit 7, and the BLC 17 is connected to a plurality of arithmetic cores (CO0 to COn) 18 and a super function unit (SFU) 19. The signal processor 11 produces a scanning line signal (sound ray signal) in which focuses of the ultrasonic echo are concentrated, and in particular a plurality of scanning lines are each produced by the assigned blocks. The plurality of arithmetic cores 18 each perform phasing addition on the element data under the control of the BLC 17. The SFU 19 performs arithmetic operations such as fast Fourier transform (FFT) and trigonometric operations. The BLC 17 controls the arithmetic operations by the plurality of arithmetic cores 18 and the SFU 19 to thereby control production of scanning line signals in each of the blocks.

The DSC 8 converts the scanning line signals produced in the signal processor 11 into image signals compatible with an ordinary television signal scanning mode (raster conversion).

The monitor 9 includes a display device such as an LCD, for example, and displays an ultrasound diagnostic image based on the image signals produced by the DSC 8.

The CPU 13 controls the components in the ultrasound diagnostic apparatus according to the instruction entered by an operator using the operating unit 14.

The operating unit 14 is provided for the operator to perform input operations and may be composed of, for example, a keyboard, a mouse, a track ball, and/or a touch panel.

The power source/battery unit 15 supplies the components in the ultrasound diagnostic apparatus with power.

The controller in the present invention comprises the CPU 13 and the BLCs 17 in the respective blocks.

Next, the configurations of the data IF unit 16, the BLIF unit 7 and the element memory 10 are described in detail.

Figure 2:
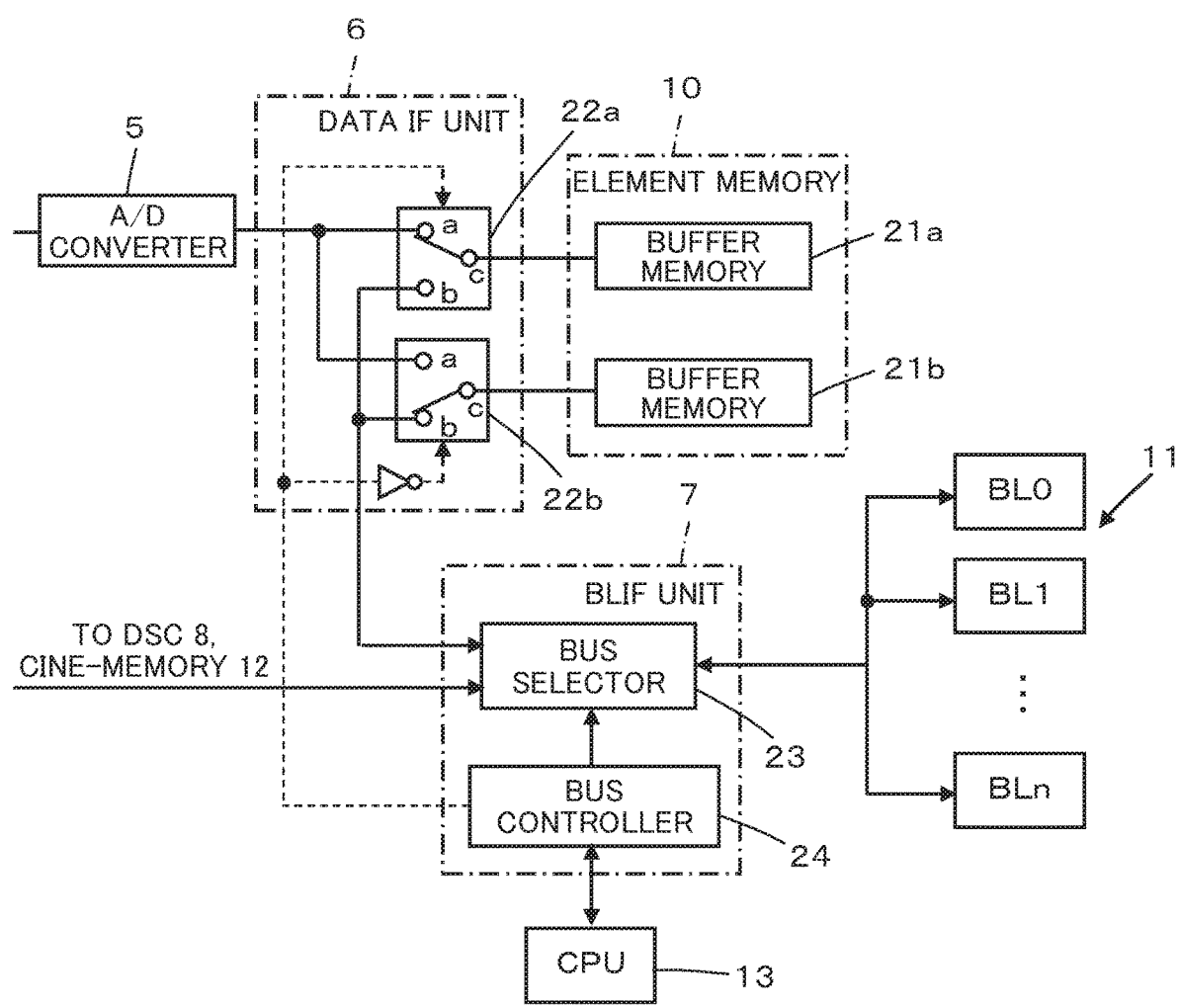
FIG. 2 is a block diagram illustrating configurations of a data IF unit, a BLIF unit and an element memory.

As illustrated in FIG. 2, the element memory 10 includes two buffer memories 21a and 21b into each of which element data of one frame is written. The data IF unit 6 connected to the element memory 10 includes a changeover switch 22a connected to the buffer memory 21a and a changeover switch 22b connected to the buffer memory 21b. The changeover switches 22a and 22b are connected to the A/D converter 5 and to a BUS selector 23 provided in the BLIF unit 7. The BUS selector 23 is connected to the respective blocks 16 in the signal processor 11, the cine-memory 12 and the DSC 8. In addition, the BLIF unit 7 includes a BUS controller 24, and the BUS controller 24 is connected to the BUS selector 23, the changeover switches 22a and 22b, and the CPU 13.

The changeover switches 22a and 22b each comprise a couple of input terminals a and b along with a single output terminal c, constituting a two-to-one changeover switch. In each of the changeover switches 22a and 22b, the input terminal a is connected to the A/D converter 5 while the other input terminal b is connected to the BUS selector 23, and the output terminal c is connected to its corresponding buffer memory 21a or 21b in the element memory 10. By having such configuration, when the input terminal a is connected to the output terminal c, element data from the A/D converter 5 can be written into the buffer memory 21a or 21b, and when the input terminal b is connected to the output terminal c on the other hand, element data can be read out from the buffer memory 21a or 21b to the signal processor 11.

The changeover switches 22a and 22b are switched over frame by frame based on the instruction signal from the BUS controller 24. For example, the BUS controller 24 outputs an instruction signal for each frame, and the instruction signal is inputted in the changeover switch 22a, while an inverted instruction signal is inputted in the changeover switch 22b. In this manner, in each of the changeover switches 22a and 22b, connection of the output terminal c to the input terminal a or b is inverted between the changeover switches 22a and 22b, and such changeover of the connection is made frame by frame. Accordingly, element data can be written into and read out from the buffer memories 21a and 21b alternately frame by frame.

Element data read out from the element memory 10 is outputted to the respective blocks in the signal processor 11 through the BUS selector 23.

Figure 3:
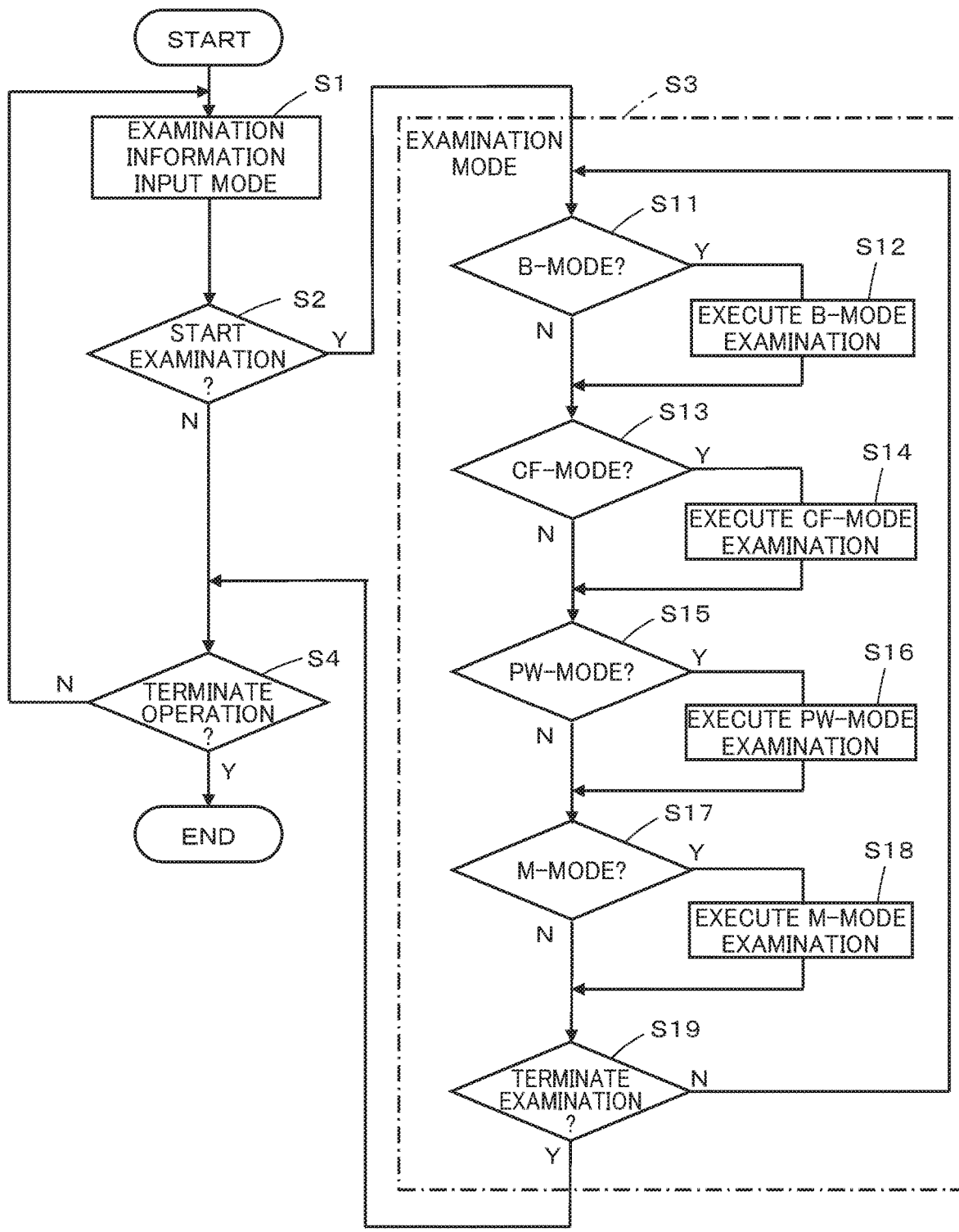
FIG. 3 is a flow chart illustrating an operation in Embodiment 1.

Next, the operation of Embodiment 1 will be described referring to the flowchart of FIG. 3.

First, once examination information including the patient information and an examination request is entered from the operating unit 14 in the examination information input mode in Step S1, the CPU 13 waits for an instruction from an operator to start the examination in Step S2. Once the instruction to start the examination is entered through the operating unit 14, the CPU 13 proceeds to Step S3 where the examination mode is executed, and thereafter waits for an instruction from the operator to terminate the examination in Step S4. When the instruction to terminate the examination is entered, a series of examination processing is terminated, leaving the process as it then stands, whereas when an instruction not to terminate but to continue the examination is entered, the operation returns to step S1 to receive examination information again.

In the examination mode in Step S3, one or more of previously set examination modes such as brightness mode (B-mode), color flow mode (CF-mode), pulsed wave mode (PW-mode), and motion mode (M-mode) may be selected to execute the ultrasound diagnosis. That is, the CPU 13 checks examination information entered in Step S1 to determine which mode has been designated and, upon verifying designation of B-mode in Step S11, the operation proceeds to Step S12 to execute examination in B-mode.

Figure 4:
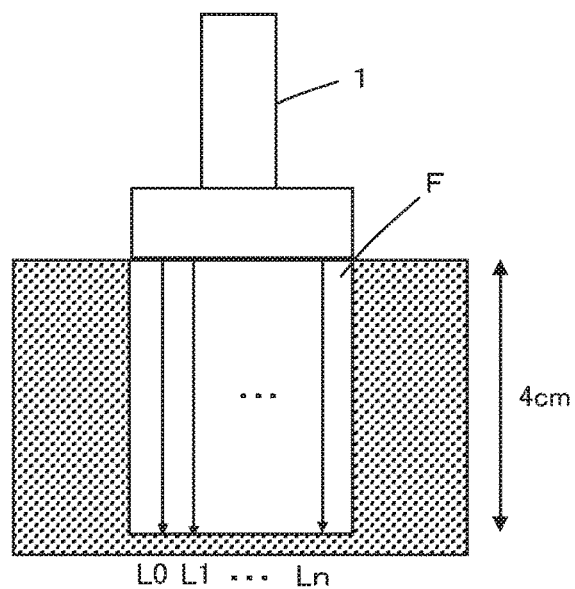
FIG. 4 is a schematic view illustrating a measurement region in a B-mode examination.
Figure 5:
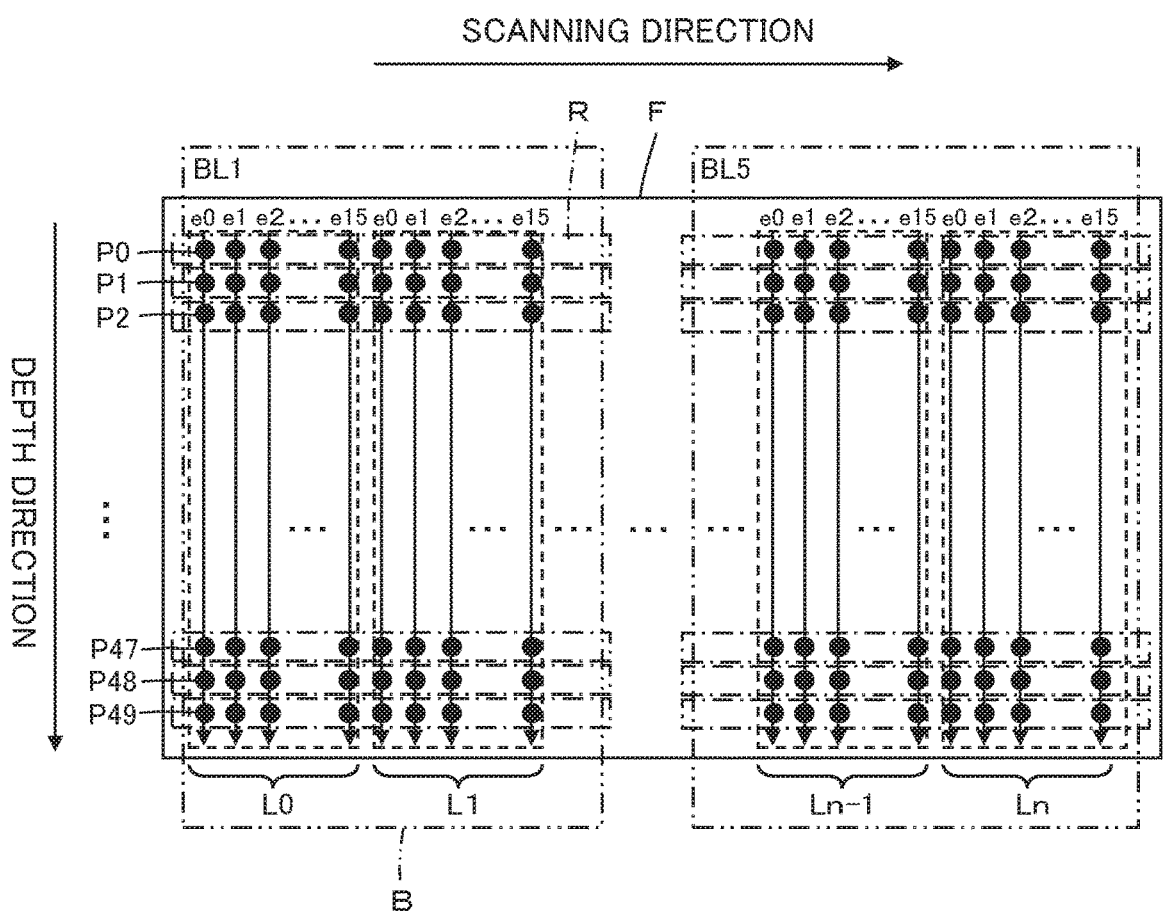
FIG. 5 is a schematic view of B-mode element data stored in an element memory.

Specifically, as illustrated in FIG. 4, the transducer array in the probe 1 sequentially transmits a B-mode ultrasonic beam toward the subject, for example, using 16 elements for one transmission, receives an ultrasonic echo from a predetermined measurement region F and outputs a reception signal, which is subjected to A/D conversion to obtain the element data in B-mode. At this time, focus points P0 to P49 are placed in the measurement region F at the depths respectively at which the measurement region F is divided into, for example, 50 regions in the depth direction, and the B-mode ultrasonic beam is sequentially transmitted from and received by the respective elements so as to form the scanning lines L0 to Ln each of which includes the focus points P0 to P49. As illustrated in FIG. 5, the B-mode element data e0 to e15 obtained so as to correspond to the focus points PO to P49 in the measurement region F is sequentially stored in the element memory 10 for each frame.

The B-mode element data stored in the element memory 10 is divided in the scanning direction, separately inputted in each of the blocks in the signal processor 11 and processed therein. In an example where the signal processor 11 has 5 blocks (BL1 to BL5), and each of the blocks has 50 arithmetic cores CO0 to CO49 constituting the arithmetic cores 18, the BLC 17 in each of the blocks divides the measurement region F into 5 regions (regions B) in the scanning direction and also into 50 regions in the depth direction so as to form 250 divisional regions R, thereafter inputs the B-mode element data contained in the 5 regions B (B-mode element data of n/5 scanning lines) into the respective blocks BL1 to BL5, and assigns the divisional regions R of the region B, whose B-mode element data has been inputted, to the arithmetic cores 18 of each of the blocks one by one. Here, the measurement region F is divided into 50 regions in the depth direction in such a manner that the resulting 50 consecutive divisional regions R in the depth direction in each of the regions B include focus points P0 to P49, respectively. In other words, the focus points are defined so as to correspond to the number of arithmetic cores 18 provided in each of the blocks.

The arithmetic cores 18 to which the divisional regions R are respectively assigned in this manner perform signal processing on the B-mode element data in each of the blocks in the depth direction in parallel and also perform signal processing on the B-mode element data in the plural blocks in the scanning direction in parallel. Specifically, 50 arithmetic cores 18 in each of the blocks perform phasing addition on the B-mode element data corresponding to the respective focus points in the assigned divisional region R in the depth direction in parallel. Similar processing is performed in the plural blocks in the scanning direction in parallel. The B-mode element data that has been subjected to phasing addition by the arithmetic cores 18 is then subjected to matching addition by the BLC 17 in each of the blocks.

In this manner, since 250 divisional regions R formed by dividing the measurement region F into 5 regions in the scanning direction and also into 50 regions in the depth direction are subjected to phasing addition in parallel, the speed of signal processing can be improved. More specifically, provided that the number of scanning lines is "n" and the number of focus points is "S", it is sufficient that n×S/250 focus points, where the number of focus points included in the n/5 scanning lines is divided by 50, are sequentially subjected to signal processing for every frame. Hence, the time required for signal processing of element data of one frame can be shortened to 1/250, compared to sequentially subjecting n×S focus points to signal processing for every frame.

Subsequently, upon verifying designation of CF-mode in Step S13, the operation proceeds to Step S14 to execute examination in CF-mode.

Figure 6:
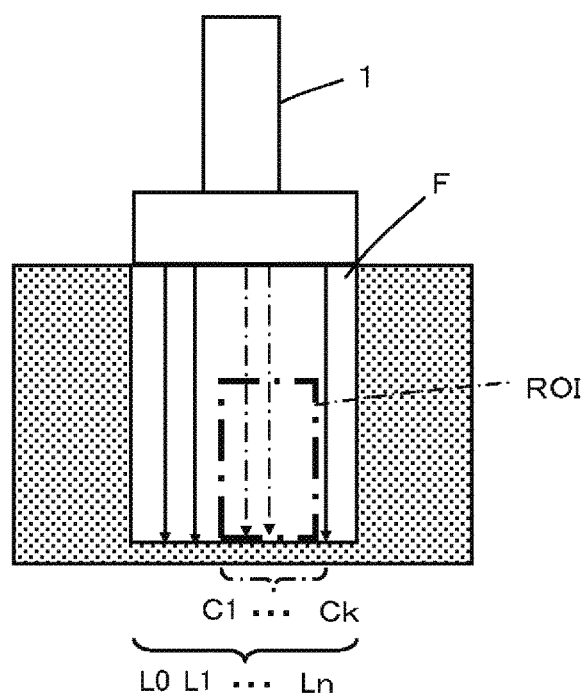
FIG. 6 is a schematic view illustrating a measurement region in the B-mode examination and a region of interest in a CF-mode examination.
Figure 7:
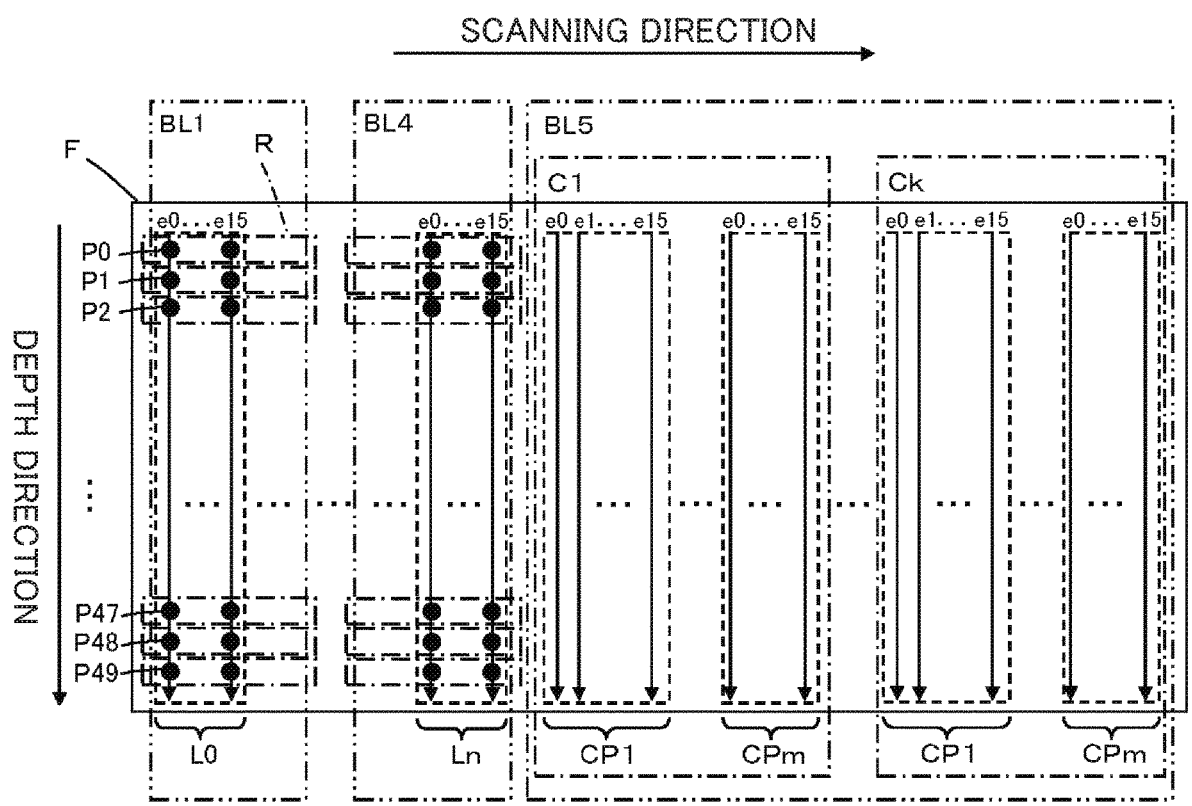
FIG. 7 is a schematic view of element data in B-mode and element data in CF-mode stored in the element memory.

In an example where B-mode as well as CF-mode are designated, a B-mode ultrasonic beam and a CF-mode ultrasonic beam are each transmitted toward and received from the subject. For transmission and reception of the CF-mode ultrasonic beam, as illustrated in FIG. 6, a region of interest ROI is defined at a predetermined location in the measurement region F by the operator, and the transducer array of the probe 1 transmits a CF-mode ultrasonic beam toward the region of interest ROI and receives an ultrasonic echo from the region of interest ROI, whereby CF-mode element data can be obtained. Here, the CF-mode ultrasonic beam is transmitted by the respective elements so as to form, in the region of interest ROI, scanning lines C1 to Ck, assuming that "k" is the number of the scanning lines, and that each scanning line is constituted with "m" packets. In the meantime, the B-mode ultrasonic beam is transmitted and received like in Step S12 to thereby obtain B-mode element data. The obtained CF-mode and B-mode element data are sequentially stored in the element memory 10 frame by frame as illustrated in FIG. 7.

The B-mode element data stored in the element memory 10 is divided into 4 regions in the scanning direction to be separately inputted in the BL1 to the BL4 of the signal processor 11, and, similarly to Step S12, is divided into 50 regions in the depth direction. The divisional regions R thus formed are separately subjected to processing by the arithmetic cores C00 to C49 in each of the blocks. In this manner, 200 divisional regions R formed by dividing the measurement region F into 4 regions in the scanning direction and also into 50 regions in the depth direction are subjected to phasing addition in parallel. Hence, provided that the number of scanning lines is "n" and the number of focus points is "S", the time required for signal processing of element data of one frame can be shortened to 1/200, compared to sequentially subjecting n×S focus points to signal processing for every frame.

Figure 8:
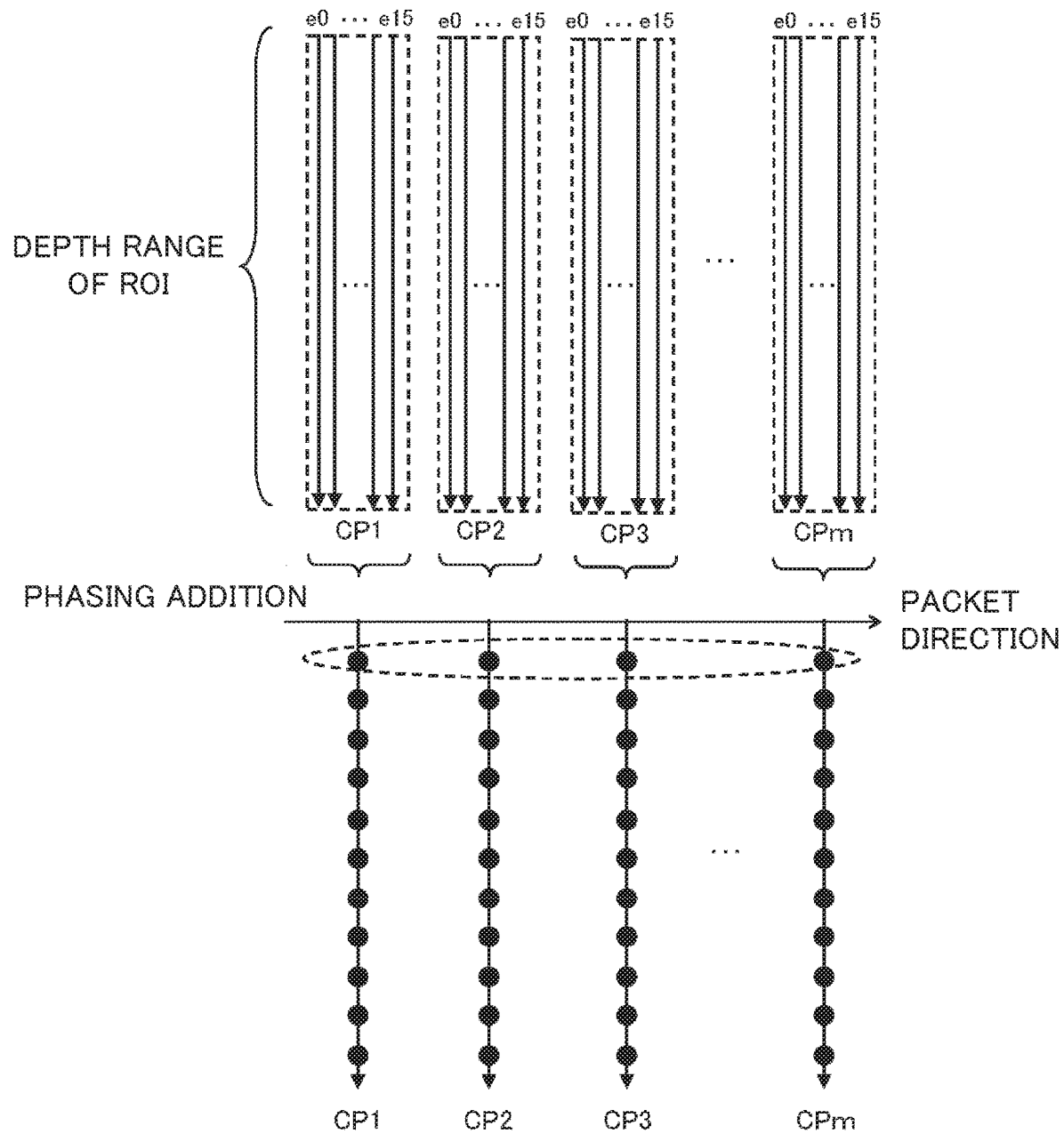
FIG. 8 is a schematic view of signal processing on element data in CF-mode.

On the other hand, CF-mode element data stored in the element memory 10 is inputted in the BL 5 through the BLC 17 therein, where CF-mode element data of every k/50 scanning lines is processed by each of the arithmetic cores 18 constituted with C00 to C049. More specifically, the arithmetic cores 18 each perform phase matching on every packet which is to constitute each of the k/50 scanning lines as illustrated in FIG. 8, to thereby produce m packet lines CP1 to CPm for each of the scanning lines. Accordingly, the packet lines CP1 to CPm are produced in each of the scanning lines C1 to Ck by the plurality of arithmetic cores 18, and the produced packet lines CP1 to CPm are subjected to autocorrelation processing or FFT processing by the SFU 19 in the packet direction, i.e., in the same depth direction. Frequency analysis in the CF-mode processing is executed in this manner.

Since B-mode element data and CF-mode element data are assigned to a plurality of blocks and are subjected to signal processing separately in parallel as described above, the processing speed can be improved. In addition, FFT processing by the SFU 19 can be performed with the increased sampling points, while the frame rate is unchanged. Hence, Doppler performance can be improved. Moreover, when improvement in the processing speed creates excess time in signal processing in the CF-mode, the number of packets can be increased. Hence, Doppler performance can be further improved.

Subsequently, upon verifying designation of PW-mode in Step S15, the operation proceeds to Step S16 to execute examination in PW-mode.

In an example where B-mode, CF-mode and PW-mode are designated, a B-mode ultrasonic beam, a CF-mode ultrasonic beam and a PW-mode ultrasonic beam are transmitted toward and received from the subject to obtain B-mode element data, CF-mode element data and PW-mode element data. The B-mode ultrasonic beam is transmitted and received like in Step S12, while the CF-mode ultrasonic beam is transmitted and received like in Step S14. The B-mode element data, the CF-mode element data and the PW-mode element data thus obtained are sequentially stored in the element memory 10 frame by frame.

The B-mode element data stored in the element memory 10 is divided into 3 regions in the scanning direction to be separately inputted in the BL 1 to the BL 3 of the signal processor 11. Then, similarly to Step S12, the B-mode element data is divided into 50 regions in the depth direction to form divisional regions R, which are respectively subjected to processing by the arithmetic cores CO0 to C49 in each of the blocks. In this manner, 150 divisional regions R formed by dividing the measurement region F into 3 regions in the scanning direction and also into 50 regions in the depth direction are subjected to phasing addition in parallel. Hence, provided that the number of scanning lines is "n" and the number of focus points is "S", the time required for signal processing of element data of one frame can be shortened to 1/150, compared to sequentially subjecting n×S focus points to signal processing for every frame.

On the other hand, CF-mode element data stored in the element memory 10 is inputted in the BL 4 through the BLC 17 therein and is separately subjected to processing by the arithmetic cores 18 constituted with CO0 to C049, similarly in Step S14.

Meanwhile, PW-mode element data stored in the element memory 10 is inputted in the BL 5 through the BLC 17 therein, is separately subjected to processing by the arithmetic cores 18 constituted with CO0 to C049 and is also subjected to FFT processing by the SFU 19. At this time, the BL 5 may include a cache memory which is not shown in the drawings, and the cache memory may maintain the PW-mode element data read out from the element memory 10, whereby the arithmetic cores 18 can perform processing on the element data repeatedly.

Since B-mode element data, CF-mode element data and PW-mode element data are subjected to signal processing separately in the plural blocks in parallel as described above, the processing speed can be improved.

Subsequently, upon verifying designation of M-mode in Step S17, the operation proceeds to Step S18 to execute examination in M-mode. The present invention enables the following operation, which is not commonly practiced.

When, for example, the B-mode, the CF-mode, the PW-mode and the M-mode are designated, through transmission and reception of an ultrasonic beam, element data in the respective modes is sequentially stored in the element memory 10 frame by frame.

B-mode element data stored in the element memory 10 is divided into 2 regions in the scanning direction to be separately inputted in the BL 1 and the BL 2 of the signal processor 11, and is divided in the depth direction to be subjected to processing separately, similarly to Step S12. In this manner, 100 divisional regions R formed by dividing the measurement region F into 2 regions in the scanning direction and also into 50 regions in the depth direction are subjected to phasing addition in parallel. Hence, provided that the number of scanning lines is "n" and the number of focus points is "S", the time required for signal processing of element data of one frame can be shortened to 1/100, compared to sequentially subjecting n×S focus points to signal processing in every frame.

In the meantime, CF-mode element data, PW-mode element data and M-mode element data stored in the element memory 10 are inputted in the BL 3 to the BL 5, respectively, and are each subjected to processing by the 50 arithmetic cores 18 in each of the blocks.

Since B-mode element data, CF-mode element data, PW-mode element data and M-mode element data are subjected to signal processing separately in the plural blocks in parallel as described above, the processing speed can be improved.

Accordingly, element data in the respective examination modes is separately subjected to signal processing by the signal processor 11, outputted to the DSC 8 through the BUS selector 23 in the BLIF unit 7, and converted to image signals. The image signals thus converted are then outputted to the monitor 9, whereby an ultrasound diagnostic image is displayed.

Figure 9:
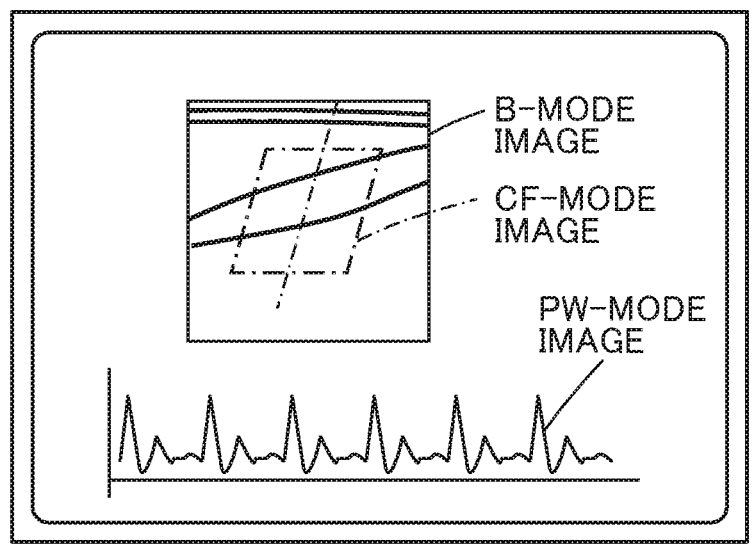
FIG. 9 is a view illustrating how a B-mode image, a CF-mode image and a PW-mode image are simultaneously displayed.

When the B-mode, the CF-mode and the PW-mode are designated in Step S16, for example, a B-mode image, a CF-mode image and a PW-mode image are simultaneously displayed, as illustrated in FIG. 9. Accordingly, when a plurality of images are simultaneously displayed, the amount of arithmetic operations increases, and the resulting decrease in the frame rate becomes a problem. However, by performing signal processing in the respective modes separately in a plurality of blocks in parallel as described above, the frame rate can be maintained to be constant.

In the examinations in the above-described Steps S12, S14, S16 and S18, element data obtained through transmission and reception of an ultrasonic beam is written into and read out from the two buffer memories 21a and 21b of the element memory 10 alternately frame by frame.

Figure 10:
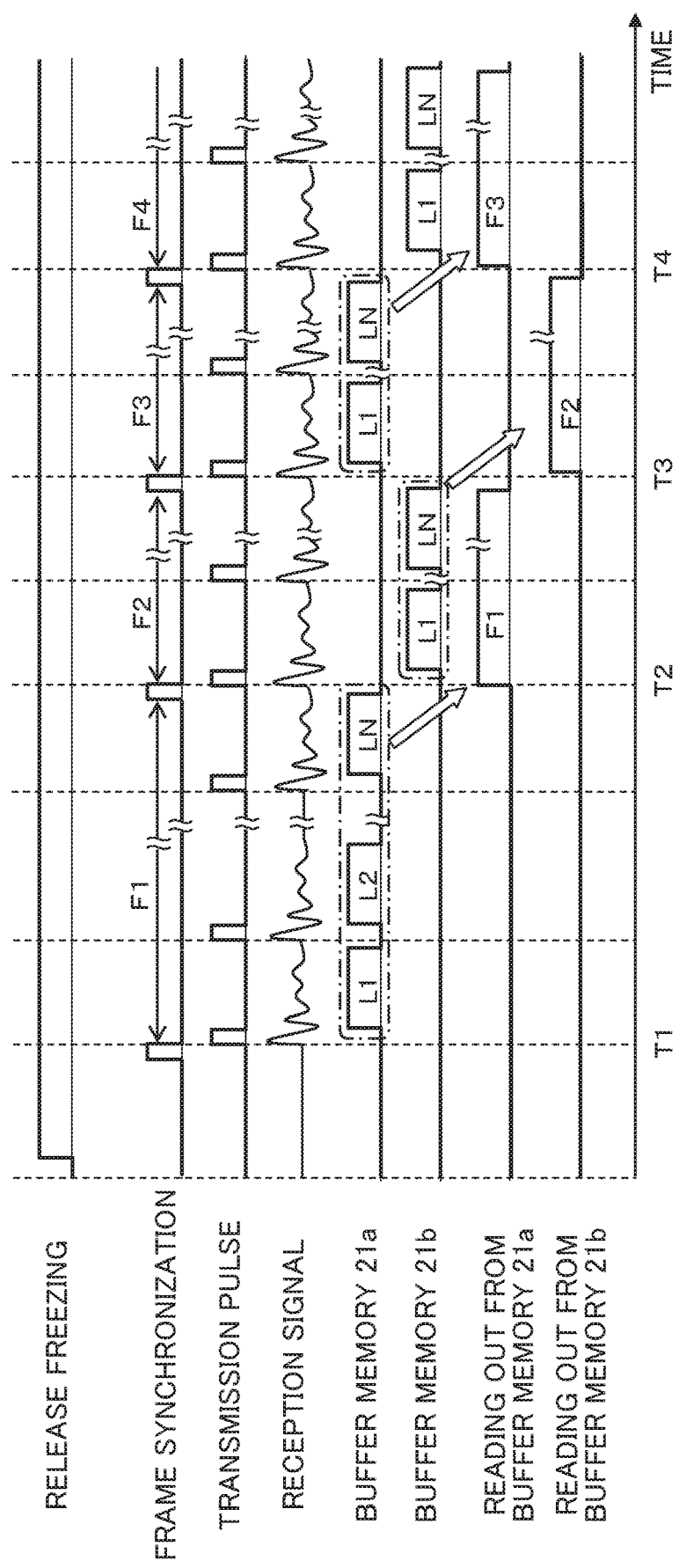
FIG. 10 is a timing chart showing writings and readings of element data into and out from two buffer memories.

For instance, in the B-mode examination, as illustrated in FIG. 10, the transmission circuit 3 transmits transmission pulses to the plurality of transducers of the probe 1 "n" times in every frame period, thereby transmitting and receiving an ultrasonic beam by the plurality of transducers. The element data obtained by subjecting the reception signals to A/D conversion is written into the buffer memories 21a and 21b of the element memory 10 alternately frame by frame.

More specifically, during the time period from T1 to T2 in which the ultrasonic beam for the frame F1 is transmitted and received, the A/D converter 5 is connected to the buffer memory 21a by the changeover switch 22a as illustrated in FIG. 2, and the element data for the frame F1 is written into the buffer memory 21a. Subsequently, during the time period from T2 to T3 in which the ultrasonic beam for the frame F2 is transmitted and received, the A/D converter 5 is connected to the buffer memory 21b by the changeover switch 22b, and the buffer memory 21a is connected by the changeover switch 22a to the signal processor 11 via the BUS selector 23. Accordingly, the element data for the frame F2 is written into the buffer memory 21b, while the element data for the frame F1 is read out from the buffer memory 21a and outputted to the signal processor 11. Further, during the time period from T3 to T4 in which the ultrasonic beam for the frame F3 is transmitted and received, the A/D converter 5 is connected to the buffer memory 21a by the changeover switch 22a, and the buffer memory 21b is connected by the changeover switch 22b to the signal processor 11 via the BUS selector 23. Accordingly, the element data for the frame F3 is written into the buffer memory 21a, while the element data for the frame F2 is read out from the buffer memory 21b and outputted to the signal processor 11.

As described above, by switching the changeover switches 22a and 22b in every frame period, element data is written into and read out from the buffer memories 21a and 21b alternately frame by frame, enabling the element data to be written into and read out from the element memory 10 in parallel. Hence, loss of time can be suppressed.

When the examinations are carried out in the respective modes as described above, and termination of examination based on the examination information for the present round of examination is verified in Step S19, the operation proceeds to Step S4.

According to this embodiment, since element data is subjected to signal processing both in the depth direction and in the scanning direction in parallel in the B-mode examination, the signal processing speed can be improved. In addition, signal processing is performed in the plural examination modes in parallel by assigning the examination modes to the respective blocks, while the signal processing is performed in the respective examination modes separately by the plurality of arithmetic cores 18 in parallel. Hence, the speed of signal processing can be improved. Moreover, since element data is written into and read out from the element memory 10 in parallel, element data is sequentially inputted into the signal processor 11, resulting in smooth progress of the signal processing.

Figure 11:
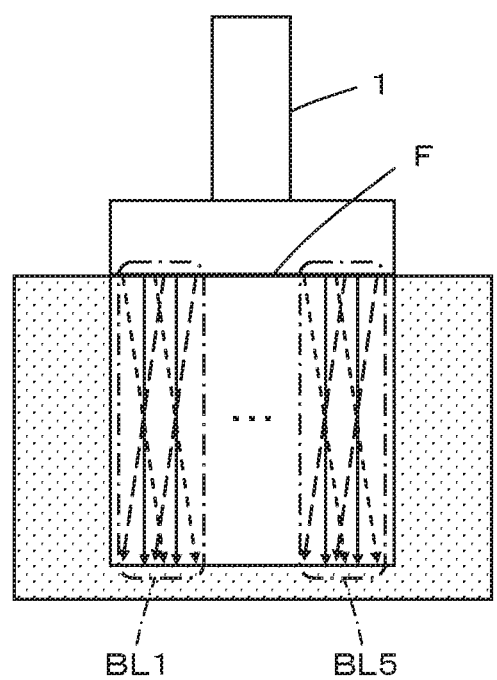
FIG. 11 is a view illustrating assignment of a plurality of blocks to a plurality of scanning lines in spatial compounding.

In the B-mode examination in the above-described Step S12, as illustrated in FIG. 11, the transmission and reception circuits may be controlled so as to transmit and receive ultrasonic waves as steering a plurality of scanning lines that have been assigned to the respective blocks, and while spatial compounding may be also performed in each of the blocks. More specifically, an ultrasonic beam being steered is transmitted to and received from the measurement region F to obtain the element data. Similarly to Step S12, the obtained element data is divided into 5 regions in the scanning direction to be inputted into the blocks, and is further divided into 50 regions in the depth direction in each of the blocks to form the divisional regions R, which are respectively subjected to signal processing by the plurality of arithmetic cores 18.

Since the element data is subjected to signal processing in the scanning direction and in the depth direction in parallel as described above, the spatial compounding speed can be improved. Moreover, the number of scanning lines can be increased when signal processing for spatial compounding yields excess time due to improvement in the processing speed, whereby the amount of information resulting from spatial compounding can be further improved.

In addition, in the above-described embodiment, element data is written into and read out from the buffer memories 21a and 21b in the element memory 10 alternately frame by frame, but more than two buffer memories 21a, 21b, . . . and 21i may be included to allow the element data to be written into and read out from them sequentially frame by frame. For example, after transmitting and receiving the ultrasonic beam for the frame F1 and writing the element data for the frame F1 into the buffer memory 21a, the ultrasonic beam for the frame F2 is transmitted and received, and the element data of the frame F2 is written into the buffer memory 21b, while the element data of the frame F1 is read out to the signal processor 11 from the buffer memory 21a. Then, during the time period for transmission and reception of the ultrasonic beam for the frame F3, the element data of the frame F3 is written into the buffer memory 21c, and the element data of the frame F2 is read out to the signal processor 11 from the buffer memory 21b. In this manner, the element data can be written into and read out from more than two buffer memories 21a, 21b, . . . and 21i sequentially frame by frame, and at the same time, the element data of one frame read out to the signal processor 11 can be assigned to a plurality of arithmetic blocks sequentially to be processed by the plurality of arithmetic cores 18.

Embodiment 2

Figure 12:
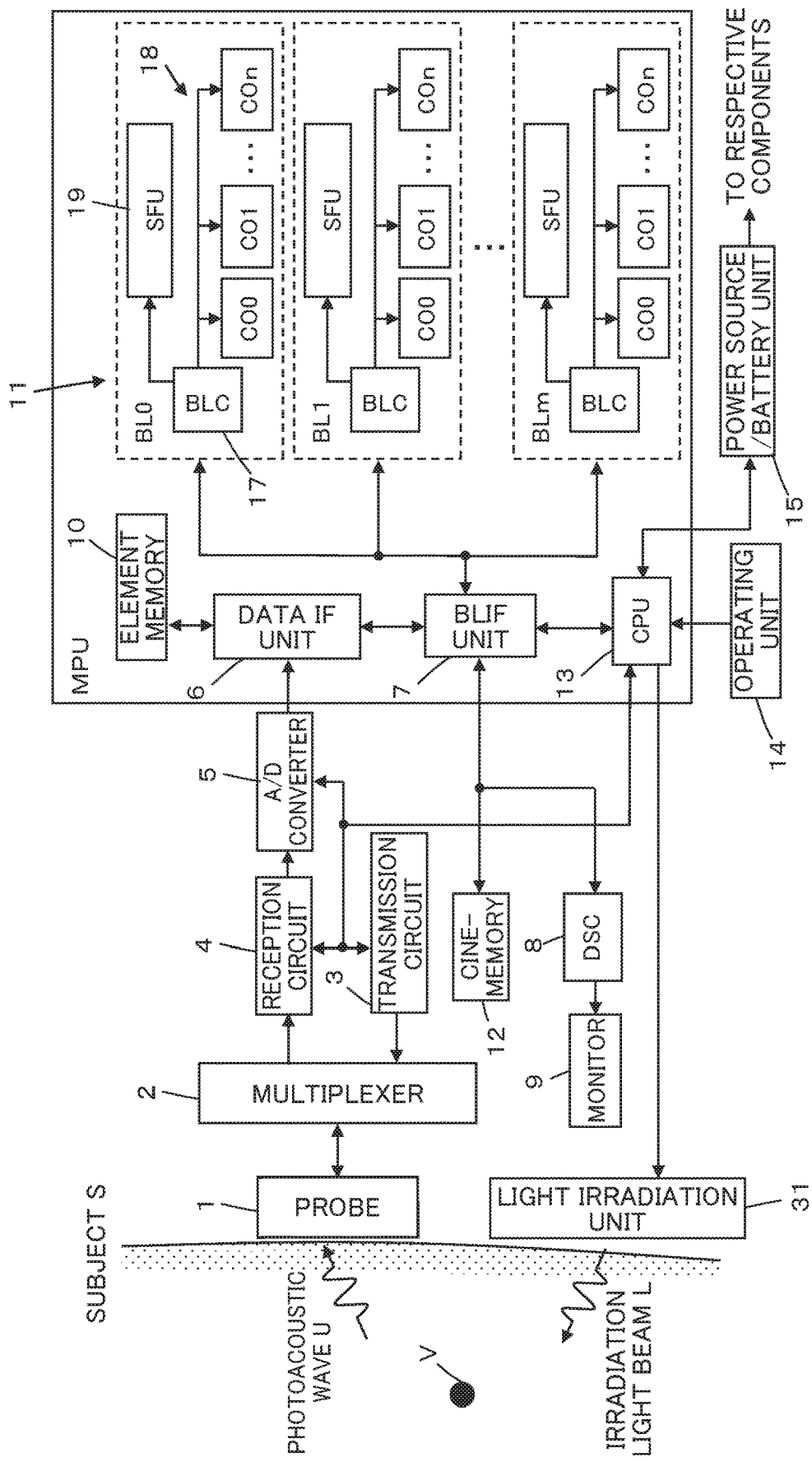
FIG. 12 is a block diagram illustrating a configuration of an ultrasound diagnostic apparatus according to Embodiment 2.

FIG. 12 illustrates a configuration of an ultrasound diagnostic apparatus according to Embodiment 2. The ultrasound diagnostic apparatus performs so-called photoacoustic imaging (PAI) to image the inside of a subject S using the photoacoustic effect. In the ultrasound diagnostic apparatus in Embodiment 1 as illustrated in FIG. 1, a light irradiation unit 31 is additionally connected to the CPU 13.

The light irradiation unit 31 sequentially emits plural irradiation light beams (energy beams) L having different wavelengths from one another toward the subject S and comprises a semiconductor laser (LD), a light emitting diode (LED), a solid laser, a gas laser or the like. The light irradiation unit 31 can use, for example, pulsed laser light beams as irradiation light beams L and emit pulsed laser light beams toward the subject S, as sequentially changing the wavelength for each pulse.

For photoacoustic imaging, under the control of the CPU 13, the light irradiation unit 31 emits irradiation light beams L toward the subject S. Once a predetermined living tissue V inside the subject S is irradiated with the irradiation light beams L emitted from the light irradiation unit 31, the living tissue V absorbs light energy of the irradiation light beams L to thereby release photoacoustic waves U (ultrasonic waves) that are elastic waves.

For example, the irradiation light beam L having a wavelength of about 750 nm and the irradiation light beam L having a wavelength of about 800 nm are emitted from the light irradiation unit 31 sequentially toward the subject S. In the meantime, oxygenated hemoglobin (hemoglobin combined with oxygen; oxy-Hb) included in plenty in a human artery has a higher coefficient of molecular absorption for the irradiation light beam L with a wavelength of 750 nm than for the irradiation light beam L with a wavelength of 800 nm. On the other hand, deoxygenated hemoglobin (hemoglobin not combined with oxygen; deoxy-Hb) included in plenty in a human vein has a lower coefficient of molecular absorption for the irradiation light beam L with a wavelength of 750 nm than for the irradiation light beam L with a wavelength of 800 nm. Accordingly, if an artery and a vein are irradiated with the irradiation light beams L having wavelengths of 800 nm and 750 nm respectively, photoacoustic waves U having intensities corresponding to the respective coefficients of molecular absorption of the artery and the vein will be released.

The photoacoustic waves U released from an artery or a vein, for example, as described above are received by the transducer array arranged in the probe 1 like in Embodiment 1, and the reception signal thereof as the element data of each frame is written into the two buffer memories in the element memory 10. The element data is written into and read out from the two buffer memories sequentially frame by frame, and the element data read out from the buffer memories is inputted into the blocks of the signal processor 11. In each of the blocks of the signal processor 11, the plurality of arithmetic cores 18 are assigned in accordance with difference in the intensities of reception signals from the living tissue V to separately perform signal processing on the element data to thereby produce image signals, and a photoacoustic image (ultrasound image) in which the living tissue V is imaged is produced based on the image signals.

The photoacoustic image is preferably displayed together with an ultrasound image obtained through transmission and reception of ultrasonic waves by the probe 1. The CPU 13 controls the transmission circuit 3 and the light irradiation unit 31 to transmit ultrasonic waves from the probe 1 and emit irradiation light beams L from the light irradiation unit 31 sequentially, enabling to display an ultrasound image and a photoacoustic image simultaneously. In a preferable example, the CPU 13 controls the transmission circuit 3 and the light irradiation unit 31 such that a photoacoustic image of one frame is produced during generation of ultrasound images of 10 frames.

According to this embodiment, since a photoacoustic image can be produced in addition to an ultrasound image, a multifaceted observation of a subject can be realized, whereby detailed diagnosis can be performed.

What is claimed is:

1. An ultrasound image producing method comprising the steps of:
  emitting an energy beam toward a subject;
  receiving by a transducer array ultrasonic waves generated from the subject upon transmission of the energy beam;
  generating element data by processing in a reception circuit a reception signal outputted from the transducer array that has received the ultrasonic waves;
  writing element data of one frame from a different frame into each of two or more buffer memories in such a manner that the two or more buffer memories correspond to frames one by one;
  producing an image signal by assigning the element data of one frame sequentially read out from the buffer memories to a plurality of arithmetic blocks, and causing each of a plurality of arithmetic cores included in the plurality of arithmetic blocks to perform processing on the element data of one frame assigned; and
  repeating writing and reading element data into and out from the two or more buffer memories frame by frame,
  wherein one examination mode or each of two or more examination modes for executing an ultrasound diagnosis selected from among previously set examination modes is assigned to the plurality of arithmetic blocks, and wherein one examination mode or two or more examination modes includes B-mode processing, a number of divisional regions according to a number of the plurality of arithmetic cores included in the arithmetic block assigned to B-mode processing is defined, by dividing a measurement region in a depth direction and a scanning direction, and the divisional regions are assigned to the arithmetic cores one by one.

2. The ultrasound image producing method according to claim 1, B-mode processing is assigned to the plurality of arithmetic blocks.

3. The ultrasound image producing method according to claim 1, wherein CF-mode processing and B-mode processing are assigned to the plurality of arithmetic blocks.

4. The ultrasound image producing method according to claim 1, wherein CF-mode processing, PW-mode processing and B-mode processing are assigned to the plurality of arithmetic blocks.

5. The ultrasound image producing method according to claim 1, wherein CF-mode processing, PW-mode processing, B-mode processing and M-mode processing are assigned to the plurality of arithmetic blocks.

6. The ultrasound image producing method according to claim 1, wherein ultrasonic waves as the energy beam are transmitted and received in different directions from one another, and the plurality of arithmetic blocks are assigned to perform spatial compounding.

7. The ultrasound image producing method according to claim 2, wherein ultrasonic waves as the energy beam are transmitted and received in different directions from one another, and the plurality of arithmetic blocks are assigned to perform spatial compounding.

8. The ultrasound image producing method according to claim 3, wherein frequency analysis in CF-mode processing is performed in each of the plurality of arithmetic blocks.

* * * * *